United States Patent
Bratkovski et al.

(10) Patent No.: US 6,624,002 B2
(45) Date of Patent: *Sep. 23, 2003

(54) BISTABLE MOLECULAR MECHANICAL DEVICES WITH AN APPENDED ROTOR ACTIVATED BY AN ELECTRIC FIELD FOR ELECTRONIC SWITCHING, GATING AND MEMORY APPLICATIONS

(75) Inventors: Alexandre M. Bratkovski, Mountain View, CA (US); Pavel Kornilovich, Mountain View, CA (US); R. Stanley Williams, Redwood City, CA (US); Xiao-An Zhang, Sunnyvale, CA (US)

(73) Assignee: Hewlett-Packard Development Company, LP., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/051,505

(22) Filed: Jan. 16, 2002

(65) Prior Publication Data

US 2002/0130317 A1 Sep. 19, 2002

Related U.S. Application Data

(60) Division of application No. 09/759,438, filed on Jan. 12, 2001, now Pat. No. 6,512,119, which is a continuation-in-part of application No. 09/738,793, filed on Dec. 14, 2000.

(51) Int. Cl.[7] ............... H01L 51/40; H01L 35/24; G11C 11/00; G11C 13/00
(52) U.S. Cl. ............... 438/99; 257/40; 365/151; 365/152
(58) Field of Search ............... 365/151, 152; 438/99; 257/40

(56) References Cited

U.S. PATENT DOCUMENTS 2,838,509 A    6/1958   Cusic et al.

(List continued on next page.)

FOREIGN PATENT DOCUMENTS

DE    10013013 A1    3/2000
FR    1.505.351      12/1967

OTHER PUBLICATIONS

Beilstein Institut Zur Foerderung Der Chemischen Wissenschaften, XP–002199088, 1988–2001, pp. 572–575.

(List continued on next page.)

*Primary Examiner*—Erik Kielin

(57) ABSTRACT

In accordance with the present invention, nanometer-scale reversible electronic switches are provided that can be assembled to make cross-bar circuits that provide memory, logic, and communications functions. The electronic switches, or crossed-wire devices, comprise a pair of crossed wires that form a junction where one wire crosses another at an angle other than zero degrees and at least one connector species connecting the pair of crossed wires in the junction. The junction has a functional dimension in nanometers, wherein at least one connector species and the pair of crossed wires forms an electrochemical cell. The connector species comprises a bistable molecule having a general formula given by

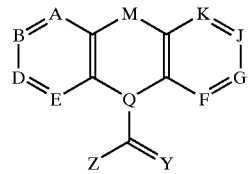

The bistable molecules evidence high switching speed. Such molecules are essentially stable against switching due to thermal fluctuations.

4 Claims, 4 Drawing Sheets

U.S. PATENT DOCUMENTS

| | | | |
|---|---|---|---|
| 3,299,122 A | | 1/1967 | Wolff et al. |
| 3,527,871 A | | 9/1970 | Engelhardt et al. |
| 3,833,894 A | * | 9/1974 | Aviram et al. ............... 365/151 |
| 6,031,756 A | | 2/2000 | Gimzewski et al. |
| 2002/0113229 A1 | * | 8/2002 | Bratkovski et al. ......... 252/500 |

OTHER PUBLICATIONS

Beilstein Institut Zur Foerderung Der Chemischen Wissenschaften, XP–002199090, 1988–2001, pp. 1–2.

Beilstein Institut Zur Foerderung Der Chemischen Wissenschaften, XP–002199091, 1988–2001, pp. 1–2.

Beilstein Institut Zur Foerderung Der Chemischen Wissenschaften, XP–002199092, 1998–2001, pp. 1–2.

Beilstein Institut Zur Foerderung Der Chemischen Wissenschaften, XP–002199093, 1988–2001, p. 1.

Beilstein Institut Zur Foerderung Der Chemischen Wissenschaften, XP–002199094, 1988–2001, pp. 1–2.

Beilstein Institut Zur Foerderung Der Chemischen Wissenschaften, XP–002199095, 1981–2001, pp. 1–2.

Beilstein Institut Zur Foerderung Der Chemischen Wissenschaften, XP–002199096, 1988–2001, pp. 1–2.

Beilstein Institut Zur Foerderung Der Chemischen Wissenschaften, XP–002199097, 1988–2001, pp. 1–2.

International Search Report, May 16, 2002, pp. 1–6, PCT/US02/00266.

* cited by examiner

BISTABLE MOLECULAR MECHANICAL DEVICES WITH AN APPENDED ROTOR ACTIVATED BY AN ELECTRIC FIELD FOR ELECTRONIC SWITCHING, GATING AND MEMORY APPLICATIONS

CROSS-REFERENCE TO RELATED APPLICATIONS

The present application is a divisional application of application Ser. No. 09/759,438. filed Jan. 12, 2001, now U.S. Pat. No. 6,512,119 B2, issued Jan. 28, 2003, which in turn is a continuation-in-part application of Ser. No. 09/738, 793 filed Dec. 14, 2000.

The present application is also related to the following applications and patents: Ser. Nos. 09/282,048 ("Chemically Synthesized and Assembled Electronic Devices"), now U.S. Pat. No. 6,459,095 B1, issued Oct. 1, 2002; 09/280,225 ("Molecular Wire Crossbar Interconnects for Signal Routing and Communications"), U.S. Pat. No. 6,314,019 B1, issued Nov. 6, 2001; 09/282,045 ("Molecular Wire Crossbar Logic")now abandoned; 09/282,049 ("Demultiplexer for a Molecular Wire Crossbar Network"), now U.S. Pat. No. 6,256,767 B1, issued Jul. 3, 2001; and 09/280,188 ("Molecular Wire Transistors"), now abandoned in favor of a first divisional application Ser. No. 09/699,080, filed Oct. 26, 2000, and a second divisional application Ser. No. 09/699,269, also filed Oct. 26, 2000, issued May 6, 2003 now U.S. Pat. No. 6,559,468, all original applications filed on Mar. 29, 1999, and U.S. Pat. No. 6,128,214, issued on Oct. 3, 2000 ("Molecular Wire Crossbar Memory").

The present application is an improvement over the foregoing applications and patent in that it utilizes a new type of switching mechanism, namely, an electric field-induced rotation of a molecular group or rotor that carries a large dipole moment.

1. Technical Field

The present invention relates generally to electronic devices whose functional length scales are measured in nanometers, and, more particularly, to simple devices used as building blocks to form more complicated structures, and to the methods for forming such devices. Devices both of micrometer and nanometer scale may be constructed in accordance with the teachings herein.

2. Background Art

The area of molecular electronics is in its infancy. To date, there has been only one convincing demonstration of a molecule acting as an electronic switch published in the open literature (see, C. P. Collier et al., *Science*, Vol. 285, pp. 391–394 (Jul. 16, 1999)), but there has been a great deal of speculation and interest within the scientific community surrounding this topic since the mid-1970s. In the published work, a monolayer film of molecules called rotaxanes were trapped between two metal electrodes and caused to switch from an ON state to an OFF state by the application of a positive bias voltage across the molecules. The ON and OFF states differed in resistivity by about a factor of 100 because of a change in the rate of tunneling through the molecules caused by oxidizing the molecules with an applied voltage.

The primary problem with the rotaxanes was that this example was an irreversible switch. It can only be toggled once. Thus, it can be used in a programmable read-only memory (PROM), but not in a ROM-like device nor in a reconfigurable system, such as a defect-tolerant communications and logic network. Rotaxanes require an oxidation and/or reduction reaction to occur before the switch can be toggled. This requires the expenditure of a significant amount of energy to toggle the switch. In addition, the large and complex nature of rotaxane molecules and related compounds potentially makes the switching times of the molecules slow.

Thus, there remains a need for a molecular species that has two stable states, which permit reversible switching from one state to the other. Such a bistable molecule must evidence rapid switching times to be of use in micro-scale and nanoscale devices.

DISCLOSURE OF INVENTION

In accordance with the present invention, nanometer-scale reversible electronic switches are provided that can be assembled to make cross-bar circuits that provide memory, logic, and communications functions. The electronic switches, or crossed-wire devices, comprise a pair of crossed wires that form a junction where one wire crosses another at an angle other than zero degrees and at least one connector species connecting the pair of crossed wires in the junction. The junction has a functional dimension in nanometers. The connector species comprises a bistable molecule having a general formula given by

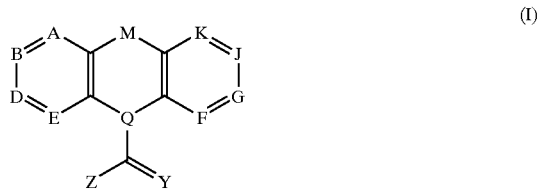

(I)

where the letters in Formula (I) are defined as follows:

A=CH; N; C-alkyl; C-halogen; C—OH; C—OR(ether); C—SR(thioether); C-amide; C-ester or thioester;

B=CH; N; C-alkyl; C-halogen; C—OH; C—OR(ether); C—SR(thioether); C-amide; C-ester or thioester;

D=CH; N; C-alkyl; C-halogen; C—OH; C—OR(ether); C—SR(thioether); C-amide; C-ester or thioester;

E=CH; N; C-alkyl; C-halogen; C—OH; C—OR(ether); C—SR(thioether); C-amide; C-ester or thioester;

F=CH; N; C-alkyl; C-halogen; C—OH; C—OR(ether); C—SR(thioether); C-amide; C-ester or thioester;

G=CH; N; C-alkyl; C-halogen; C—OH; C—OR(ether); C—SR(thioether); C-amide; C-ester or thioester;

J=CH; N; C-alkyl; C-halogen; C—OH; C—OR(ether); C—SR(thioether); C-amide; C-ester or thioester;

K=CH; N; C-alkyl; C-halogen; C—OH; C—OR(ether); C—SR(thioether); C-amide; C-ester or thioester;

M=$CH_2$; $CF_2$; $CCl_2$; $CHOCH_3$; CHOH; CHF; CO; CH=CH; $CH_2$—$CH_2$; S; O; NH; NR; NCOR; or NCOAr;

Q=CH; nitrogen; phosphorus; or boron;

Y=O or S; and

Z=R (H; alkyl); NHR; OR; SR; CHR—NHR; CHR—OR; CHR—SR; CHR—X (halogen); NR—NHR; NR—OR; or NR—SR.

The bistable molecules evidence high switching speed. Such molecules are essentially stable against switching due to thermal fluctuations.

BRIEF DESCRIPTION OF THE DRAWINGS

FIG. 1b is a perspective elevational view, depicting the device shown in FIG. 1a;

FIGS. 2a and 2b are ball-and-stick drawings that depict a molecule which has been designed with an appended rotor perpendicular to the orientation or current-carrying axis of the entire molecule, wherein FIG. 2a depicts the molecule in one stable state and FIG. 2b depicts the same molecule in a second stable state; and FIGS. 3a–3c, on coordinates of current and voltage, are plots depicting a generic hysteresis loop for the type of molecule shown in FIGS. 2a–2b, wherein FIG. 3a depicts the I-V characteristic in one stable orientation with respect to the rotor, FIG. 3b depicts the I-V characteristic when the rotor is flipped to the second stable state, and FIG. 3c depicts the full hysteresis loop.

BEST MODES FOR CARRYING OUT THE INVENTION

Definitions

As used herein, the term "self-aligned" as applied to "junction" means that the junction that forms the switch and/or other electrical connection between two wires is created wherever two wires, either of which may be coated or functionalized, cross each other, because it is the act of crossing that creates the junction.

The term "self-assembled" as used herein refers to a system that naturally adopts some geometric pattern because of the identity of the components of the system; the system achieves at least a local minimum in its energy by adopting this configuration.

The term "singly configurable" means that a switch can change its state only once via an irreversible process such as an oxidation or reduction reaction; such a switch can be the basis of a programmable read-only memory (PROM), for example.

The term "reconfigurable" means that a switch can change its state multiple times via a reversible process such as an oxidation or reduction; in other words, the switch can be opened and closed multiple times, such as the memory bits in a random access memory (RAM).

The term "bi-stable" as applied to a molecule means a molecule having two relatively low energy states separated by an energy (or activation) barrier. The molecule may be either irreversibly switched from one state to the other (singly configurable) or reversibly switched from one state to the other (reconfigurable).

Micron-scale dimensions refers to dimensions that range from 1 micrometer to a few micrometers in size.

Sub-micron scale dimensions refers to dimensions that range from 1 micrometer down to 0.05 micrometers.

Nanometer scale dimensions refers to dimensions that range from 0.1 nanometers to 50 nanometers (0.05 micrometers).

Micron-scale and submicron-scale wires refers to rod or ribbon-shaped conductors or semiconductors with widths or diameters having the dimensions of 1 to 10 micrometers, heights that can range from a few tens of nanometers to a micrometer, and lengths of several micrometers and longer.

Basic Information on Crossed Wire Switches

Figure 1A:
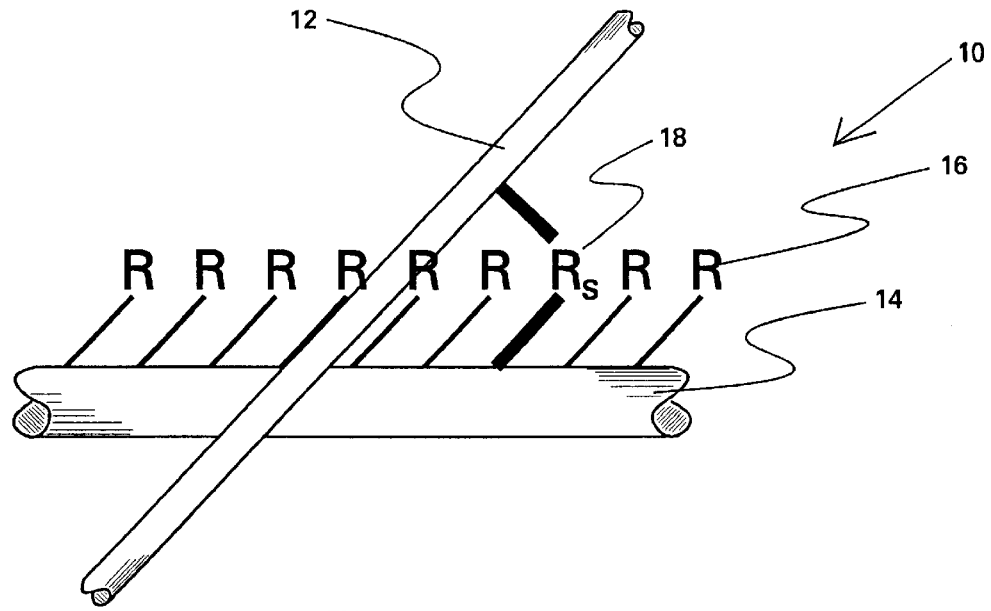
FIG. 1a is a schematic representation of two crossed wires, with at least one molecule at the intersection of the two wires.
Figure 1B:
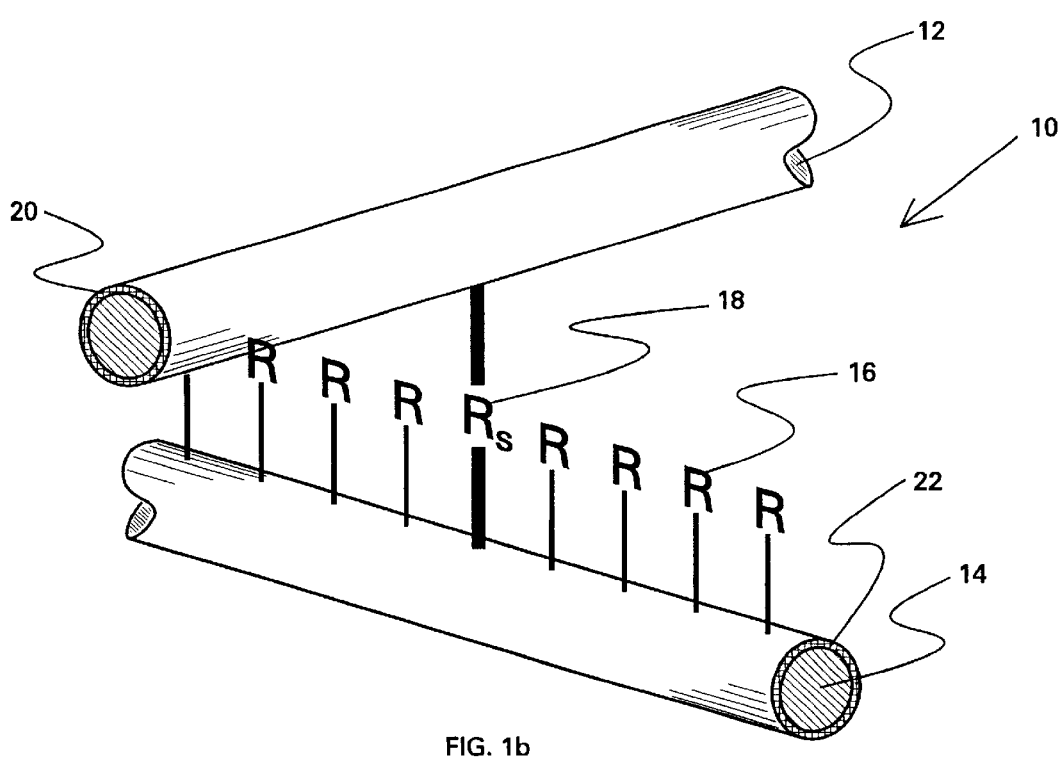

The essential device features are shown in FIGS. 1a–1b. A crossed wire switch 10 comprises two wires 12, 14, each either a metal or semiconductor wire, that are crossed at some non-zero angle. In between those wires is a layer of molecules or molecular compounds 16, denoted R in FIGS. 1a and 1b. The particular molecules 18 (denoted $R_s$) that are sandwiched at the intersection of the two wires 12, 14 are identified as switch molecules, also interchangeable referred to herein as a junction. When an appropriate voltage is applied across the wires, the switch molecules are either oxidized or reduced. When a molecule is oxidized (reduced), then a second species is reduced (oxidized) so that charge is balanced. These two species are then called a redox pair. One example of this device would be for one molecule to be reduced, and then a second molecule (the other half of the redox pair) is oxidized. In another example, a molecule is reduced, and one of the wires is oxidized. In a third example, a molecule is oxidized, and one of the wires is reduced. In a fourth example, one wire is oxidized, and an oxide associated with the other wire is reduced. In all cases, oxidation or reduction will affect the tunneling distance or the tunneling barrier height between the two wires, thereby exponentially altering the rate of charge transport across the wire junction, and serving as the basis for a switch.

The electrical tasks performed by these devices are largely determined by the types of wires (electrodes) and the interwire materials that are used. Table I presents the various types of devices that might be fabricated from various combinations of the wires 12, 14 in FIGS. 1a–1b.

TABLE I

Wire (Electrode) Materials

| Device Type | Metal-metal (same) | Metal-metal (different) | Metal-semiconductor | Semiconductor-Semiconductor (p-n junction) | Semiconductor-semiconductor (heterojunction) |
|---|---|---|---|---|---|
| Resistor | X | X | X | | |
| Tunneling resistor | X | X | X | | |
| Resonant tunneling resistor | X | X | X | | |
| Diode | | X | X | X | X |
| Tunneling diode | | X | X | X | X |
| Resonant tunneling diode | | X | X | X | X |
| Battery | | X | X | | X |

Depending on the molecules or materials that are used between the wires (the electrodes), each junction can either display the types of electrical function described below immediately on contact of the wires or the junction can have a switching function that acts to connect or disconnect the two wires together electrically. This switch can either be singly configurable or reconfigurable. In the first case, the initial state of the switch is open or closed. Electrically biasing the switch beyond a particular threshold voltage that is determined by the materials in the junction, which is essentially an electrochemical cell, oxidizes or reduces the material or molecules between the wires to irreversibly close or open the switch, respectively, thus permanently reversing its initial state. In the second case, by cycling the polarity and magnitude of the voltage on the switch beyond the appropriate threshold values, it is possible to reversibly oxidize or reduce the properly selected materials or molecules to close or open the switch many times. In either case, when closed, the type of electrical connection that is made between the wires depends upon the materials from which the wires (or electrodes) are fabricated as well as the identity of the molecules or materials between the wires.

Table I above shows a matrix of the various types of functions that can be obtained from various combinations of electrode materials and materials or molecules used in the junction. A resistor has a linear current-voltage characteristic, and is made by intentionally over-reducing the junction between various types of wires to essentially form a short circuit between the wires. The opposite of this process is to over-oxidize a junction, which will consume the wire in a localized region and effectively break the wire (create an open circuit) in that wire at the position of the junction. A tunneling resistor maintains a thin, approximately 2 nanometer thick, insulating barrier between wires and has an exponential current-voltage characteristic. In the case that junction molecules or materials have a sharply defined energy state inside the band gap of an electrically insulating barrier that can be accessed by electrically biasing the junction, the connection between the wires can exhibit a flow of electrical current that is dominated by the process of resonant tunneling. The resonant tunneling can produce one or more inflection points in the otherwise exponential current-voltage characteristic of a tunneling resistor. A diode is a junction that passes current more easily in one direction than in the other, and thus has an asymmetry in the current-voltage characteristic for positive and negative voltages. A tunneling diode has both the positive-negative voltage asymmetry of the diode and the exponential current-voltage characteristic of the tunneling resistor. A resonant tunneling diode has a positive-negative voltage asymmetry plus it has a peak in its current-voltage characteristic, such that over a restricted range of increasing magnitude of the voltage the magnitude of the current actually decreases, a phenomenon that is known as negative differential resistivity. Finally, a battery is a circuit element that acts to hold a constant voltage difference between its electrodes as long as the battery is sufficiently charged, e.g., there is a sufficient supply of oxidizing and reducing agents separated by an insulating barrier. Charging the battery is accomplished by placing the appropriate voltage across the junction, which as stated before is an electrochemical cell, to only partially oxidize or reduce the material or molecules in the junction. In general, any real junction between wires formed by the processes described above will actually have two or more of the electrical functions described, with the effective circuit elements connected in series.

Thus, the present invention may be executed with any number of metallic or semiconducting wire/molecule combinations, depending on the device properties desired from the assembled circuit.

Basic Information on Fabrication of Wire Electrodes

Process-Defined Wires (defined as wires that are prepared by conventional electronic-circuit processing techniques; wires are typically prepared on a substrate as part of a circuit):

Metallic and semiconductor wires, with diameters ranging from several micrometers to a single micrometer (defined as micrometer-scale), or with diameters ranging from a single micrometer down to 40 nanometers (defined as sub-micrometer scale) in diameter, may be prepared using well-established art, including lithographic (optical, ultraviolet, or electron beam) technologies. These wires normally have a ribbon shape or rectangular cross section, although circular cross sections are not precluded, with the width of the wire being determined by the lithographic process used to define the wire and its height being defined by the amount of material deposited in the region defined by lithography.

Chemically-Prepared Wires (these wires are prepared by techniques other than conventional electronic processing technology; wires are typically prepared as a bulk material, rather than as part of a circuit board):

Metal and semiconductor nanowires are defined as wires with diameters below 50 nanometers (typically 2 to 20 nanometers), and with lengths in the range of 0.1 micrometers to 50 micrometers (typically 5 to 10 micrometers). These may be prepared chemically using any one of a number of techniques described in the references given below.

One example of a reported technique for the production of semiconductor nanowires of the semiconducting element germanium is to react germanium tetrachloride and phenyltrichlorogermanium with a dispersion of sodium metal in the solvent toluene, and at a temperature near 300° C. in a closed vessel, under an inert environment, for a period of several days. That preparation produces single-crystal germanium nanowires of diameters three to thirty nanometers, and of lengths from 0.5 to 10 micrometers.

A second example of a reported technique for the production of semiconductor nanowires of the semiconducting element silicon, is to laser vaporize a target containing elemental silicon and iron. The target is placed in a vacuum oven at 1300° C., and an inert gas is flowed through the oven during the vaporization process. This technique produces silicon wires that have diameters in the range of 20 to 30 nanometers, and lengths ranging from 1 to 20 micrometers.

One example of a reported technique for the production of metallic nanowires of the metallic element gold is to electrochemically grow gold wires within the pores of an anodically etched aluminum oxide thin film. The aluminum oxide is dissolved in acidic solution, releasing the gold nanowires, which are then collected. Gold nanowires grown in this manner are characterized by diameters ranging from 20 to 30 nanometers, and lengths ranging from 0.5 to 5 micrometers.

Nanowires of various metallic and semiconducting materials may be prepared in a variety of fashions. Some of these devices will require doped semiconductor wires, such as doped Si.

For the case of Si wires, the wires can be doped when the wires are physically prepared. In this case, it is necessary to add the dopant into the reaction vessel as the wires are formed. For example, in the laser ablation/vacuum oven preparation technique described above, a small amount of dopant gas, such as phosphorus trihydride ($PH_3$) or arsenic trihydride ($AsH_3$) is added into the inert gas (argon, for example) that flows through the vacuum oven during the laser ablation/wire formation process.

Conversely, these wires can be modulation-doped by coating their surfaces with appropriate molecules—either electron-withdrawing groups (Lewis acids, such as boron trifluoride ($BF_3$)) or electron-donating groups (Lewis bases, such as alkylamines) to make them p-type or n-type conductors, respectively. See wire preparation routes listed below. FIG. 1b depicts a coating 20 on wire 12 and a coating 22 on wire 14. The coatings 20, 22 may be modulation-doping coatings, tunneling barriers (e.g., oxides), or other nano-scale functionally suitable materials. Alternatively, the wires 12, 14 themselves may be coated with one or more R species 16, and where the wires cross, $R_s$ 18 is formed. Or yet alternatively, the wires 12, 14 may be coated with molecular species 20, 22, respectively, for example, that enable one or both wires to be suspended to form colloidal suspensions, as discussed below.

To dope the wires via modulation-doping, it is necessary to chemically functionalize the surface of the wires using organic or inorganic molecules that will covalently bind to the Si—O—H groups at the surface of the wires. When silicon nanowires are exposed to air, a thin surface layer (1 nm) of $SiO_2$ will naturally form, and at the $SiO_2$/air interface, the $SiO_2$ surface is terminated by Si—O—H bonds. Groups that will bind to or replace Si—O—H groups are not limited to but include R—$Si(CH_3)_x(OCH_{3-x})$, R—Si$(CH_3)_x(OCH_2CH_{3-x})$, R—$Si(CH_3)_xCl_{3-x}$, and others. In this case, R represents an organic or inorganic moiety that can contain electron-withdrawing (a Lewis acid) or electron-donating groups (a Lewis base). This chemistry of binding molecules to a $SiO_2$ passivated silicon surface is well established. One published example reaction for binding molecules to the surface of $SiO_2$ passivated silicon is:

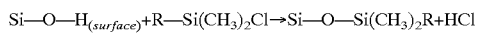

Other semiconductor wires can be functionalized with organo-amines, organo-thiols, organo-phosphates, etc.

Apparently, no previous description of how to modulation-dope chemically synthesized semiconductor wires has yet appeared in the technical literature.

For the case of other nanowires, such as metal nanowires, the wires can be chemically functionalized with R—SH (for gold or silver wires), or R—$NH_2$ (for platinum wires and palladium wires), or R—$CO_2H$ for other metals such as $Al_2O_3$-coated aluminum wires or titanium wires), where the R-group denotes some organic moiety that will lend the wire certain chemical properties—such as the property that will allow the person skilled in the art to disperse the wires, as a colloid, in a solvent. In one example, gold wires might be functionalized with dodecanethiol ($C_{12}H_{25}SH$). The dodecanethiol not only will provide the wires with a thin surface tunneling barrier, but will also allow for the wires to be dispersed in simple organic solvents, such as hexane or chloroform.

Basic Information on Wire Preparation Routes

The following materials may be prepared as nanowires according to the reference listed.

Silicon: A. M. Morales et al, "A laser ablation method for the synthesis of crystalline semiconductor nanowires", *Science*, Vol. 279, pp. 208–211 (Jan. 9, 1998).

Germanium: J. R. Heath et al, "A liquid solution synthesis of single crystal germanium quantum wires", *Chemical Physics Letters*, Vol. 208, pp. 263–268 (Jun. 11, 1993).

Metal Nanowires: V. P. Menon et al, "Fabrication and Evaluation of Nano-electrode Ensembles", *Analytical Chemistry*, Vol. 67, pp. 1920–1928 (Jul. 1, 1995).

Functionalizing Silicon: T. Vossmeyer et al, "Combinatorial approaches toward patterning nanocrystals", *Journal of Applied Physics*, Vol. 84, pp. 3664–3670 (Oct. 1, 1998) (one of a number of references).

Functionalizing the Surfaces of Gold Nanostructures: D. V. Leff et al, "Thermodynamic Size Control of Au Nanocrystals: Experiment and Theory", *The Journal of Physical Chemistry*, Vol. 99, p. 7036–7041 (May 4, 1995).

Molecular switching components may come from any number of different classes of molecules, depending, again, on the desired properties of the device. The key requirement of the molecules is that, when they are sandwiched between two wires, they may be electrochemically modified (i.e. oxidized or reduced) by applying a voltage across the wires. When the molecular components are so modified, the net effect is that the tunneling barrier between the two wires is modified, and the rate of current flow is changed. This forms the basis of a switch that can, in turn, be used for memory, logic operations, and communication and signal routing networks. Molecular switches can include redox pairs of molecules, in which application of a voltage reduces one of the molecules and oxidizes the other. An example of such a molecular redox pair might be: nickelocene (dicyclopentadienyl nickel), or $Cp_2Ni$, with tetrabutylammonium hexafluorophosphate ($Bu_4NPF_6$). The reaction, then, would be:

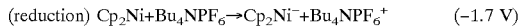

or

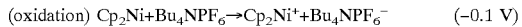

The nickelocene system is of particular interest in that the reduction, as probed by solution phase cyclic voltammetry, is highly asymmetric. Such asymmetry is analogous to magnetization hysteresis curves that form the basis for stable and rewriteable magnetic memory. However, in the presence of oxygen, the reduction of nickelocene is irreversible, as probed by solution phase voltammetry. In either case, reduction or oxidation of this system will modify the tunneling barrier between the two wires between which the molecules are sandwiched. Thus, this system could operate as either a reconfigurable, or a singly configurable molecular switch. For metallocene systems, see, e.g., J. D. L. Holloway et al, "Electron-transfer reactions of metallocenes: Influence of metal oxidation state on structure and reactivity", *Journal of the American Chemical Society*, Vol. 101, pp. 2038–2044 (Apr. 11, 1979).

The connector species 16 comprises a material that displays a significant, or measurable, hysteresis in its current-voltage curve, obtained either from solution electrochemistry or from current-voltage characteristics in a solid-state junction. Examples of such species include metalocenes, rotaxanes, pseudo-rotaxanes, and catenanes, which rely on intramolecular hydrogen bonding. While such molecules are useful for the purpose disclosed, however, simple intramolecular hydrogen bonding forces are relatively easily exceeded under certain conditions, as discussed above.

Present Invention

The present invention utilizes a new type of switching mechanism, an electric field-induced rotation of a molecular group or rotor that carriers a large dipole moment. Thus, the molecule is neither oxidized nor reduced in the toggling of the switch, which potentially avoids initiating a nonreversible reaction. The part of the molecule that moves is quite small, so the switching time should be very fast, on the order of 1 ps. Also, the molecules are much simpler and thus easier and cheaper to make than the rotaxanes and related compounds.

The present invention turns molecules into active electronic devices that can be switched with an external electric field. The general idea is to synthesize molecules with a stationary part that will bridge two electrodes (stator) and a conformationally bistable group (rotor) that has a large dipole moment. The molecule is designed such that intramolecular forces, such as hydrogen bonding, as well as steric repulsions, stabilize the rotor asymmetrically with respect to the stator. The stator is designed to be symmetric with respect to the rotation axis of the rotor. Therefore, there always are two particular orientations of the rotor that are stable but have a large energy barrier to flip from one state to the other (see FIGS. 2a–2b). The height of the barrier is required to be sufficiently larger than the operation temperature of the device so that the switch will not be activated by random thermal fluctuations. Under these conditions, when the rotor is put into a particular orientation, it will remain there and will not accidentally switch to the alternate stable state. However, the switching can be done with an external field by applying a bias voltage between the two electrodes. The dipole moment of the rotor will tend to align parallel to the external field exerted on the molecule. If the initial direction of the dipole is opposite to that of the applied field, then it will be forced to rotate with respect to the stator and switch to the second stable state at some threshold bias voltage. The rotor will remain in that state until an external field of sufficient magnitude is applied in the opposite direction.

Formula (I) below represents a switchable molecule with a single active (switchable) dipole group, kept in the particular configuration by hydrogen bonding to sites E or D:

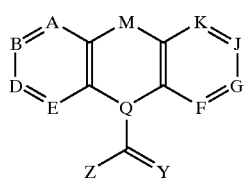

(I)

The letters in Formula (I) are defined as follows:

A=CH; N; C-alkyl; C-halogen; C—OH; C—OR(ether); C—SR(thioether); C-amide; C-ester or thioester;

B=CH; N; C-alkyl; C-halogen; C—OH; C—OR(ether); C—SR(thioether); C-amide; C-ester or thioester;

D=CH; N; C-alkyl; C-halogen; C—OH; C—OR(ether); C—SR(thioether); C-amide; C-ester or thioester;

E=CH; N; C-alkyl; C-halogen; C—OH; C—OR(ether); C—SR(thioether); C-amide; C-ester or thioester;

F=CH; N; C-alkyl; C-halogen; C—OH; C—OR(ether); C—SR(thioether); C-amide; C-ester or thioester;

G=CH; N; C-alkyl; C-halogen; C—OH; C—OR(ether); C—SR(thioether); C-amide; C-ester or thioester;

J=CH; N; C-alkyl; C-halogen; C—OH; C—OR(ether); C—SR(thioether); C-amide; C-ester or thioester;

K=CH; N; C-alkyl; C-halogen; C—OH; C—OR(ether); C—SR(thioether); C-amide; C-ester or thioester;

M=CH$_2$; CF$_2$; CCl$_2$; CHOCH$_3$; CHOH; CHF; CO; CH=CH; CH$_2$—CH$_2$; S; O; NH; NR; NCOR; or NCOAr;

Q=CH; nitrogen; phosphorus; or boron;

Y=O or S; and

Z=R (H; alkyl); NHR; OR; SR; CHR—NHR; CHR—OR; CHR—SR; CHR—X (halogen); NR—NHR; NR—OR; or NR—SR.

One possible synthetic route for the preparation of molecules having Formula I is shown below. Starting compounds II and III can be reacted via condensation-cycloaddition followed by necessary reduction to form an intermediate compound III. Compounds II and III are commercially available. Intermediate II is then reacted with Z(Y=)C—X under base conditions to form Compound I, as illustrated.

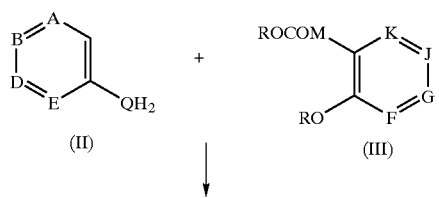

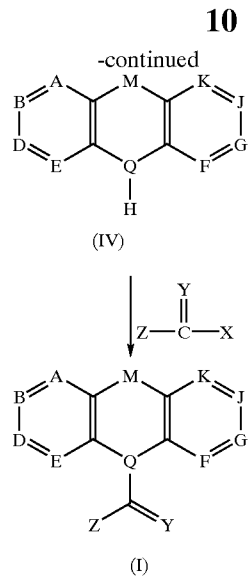

(IV)

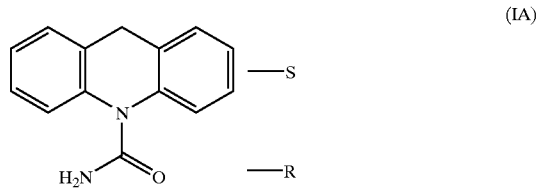

(I)

Figure 2B:
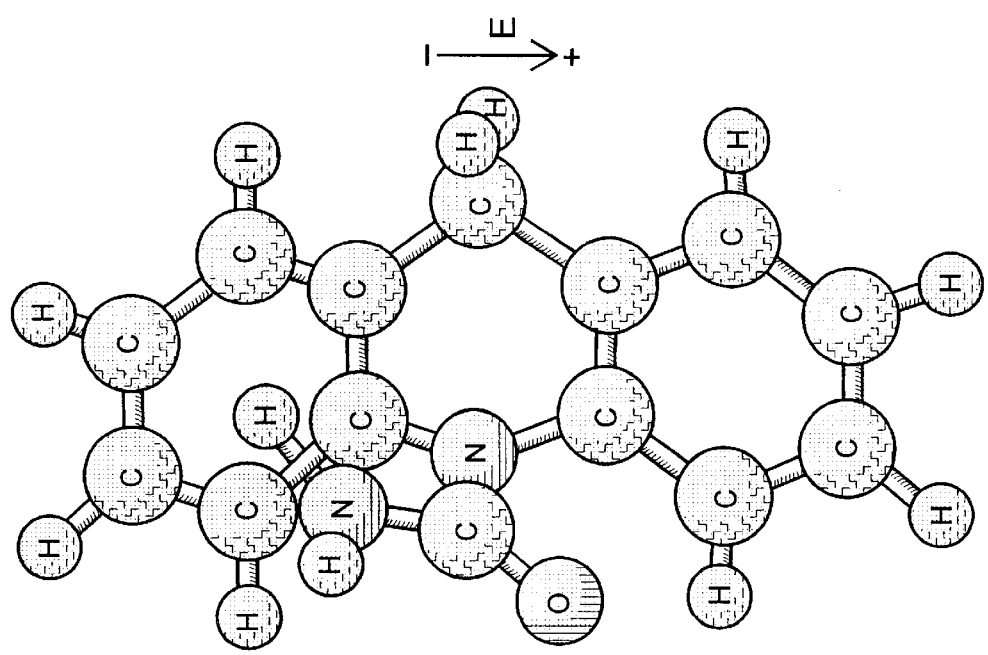
Figure 2A:
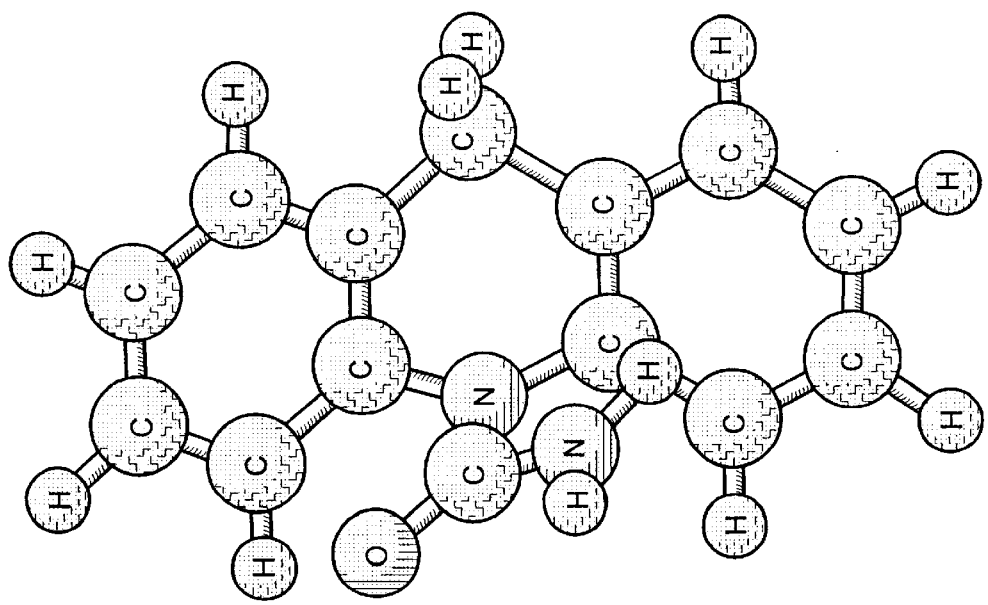

Turning now to FIGS. 2a–2b, the molecule depicted therein is seen to have the formula (IA)

The molecule depicted in Formula (IA) is designed with a stator portion S and an appended rotor R perpendicular to the orientation or current-carrying axis of the entire molecule; that is, from left to right or vice versa, as shown above.

In FIGS. 2a–2b, the molecule is shown rotated 90 degrees from the representation above, and in this case, the external field is applied along the orientation axis of the molecule (vertical direction) as pictured—the electrodes are oriented in the horizontal direction and perpendicular to the plane of the paper. Application of an electric field oriented from bottom to top in FIG. 2a will cause the rotor R as pictured in FIG. 2a to rotate to the position shown in FIG. 2b. Application of the electric field from the top to the bottom in FIG. 2b will cause R to rotate from the position shown in FIG. 2b to that shown in FIG. 2a. Switching from one stable state to the other stable state is reversible, but is not readily affected by thermal fluctuations, having a barrier to switching of about 0.3 eV or more.

Figure 3C:
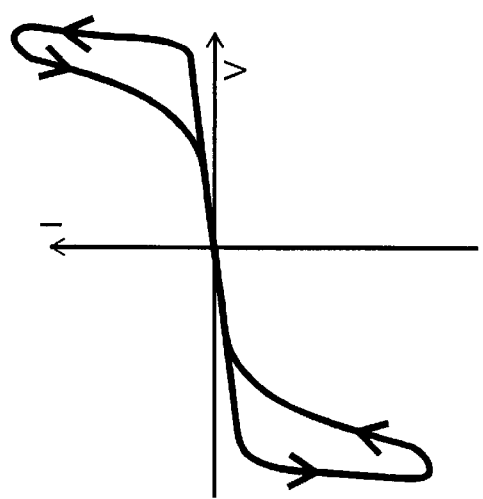
Figure 3B:
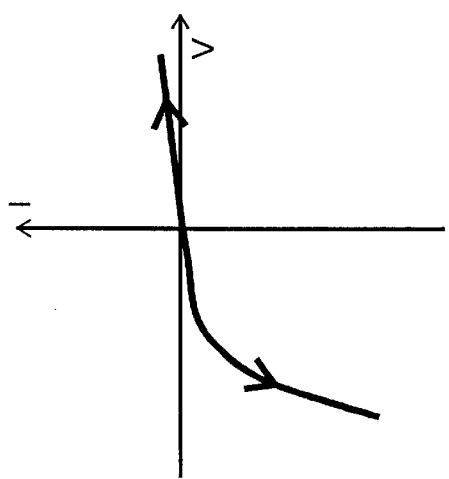
Figure 3A:
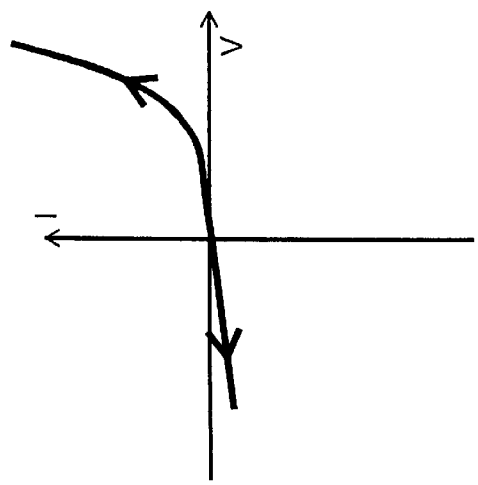

A key component of the molecular design is that the asymmetric mutual orientation of the rotor and stator and their strong interaction will yield an asymmetric diode-like current-voltage (I-V) characteristic; see FIG. 3a, which depicts the I-V characteristic of the molecule when the rotor is in one stable orientation with respect to the stator.

The I-V characteristic will invert with respect to the applied voltage when the field across the molecule causes the rotor to reverse its orientation; see FIG. 3b, which depicts the I-V characteristic when the rotor is flipped to the second stable state.

The I-V characteristic of the bistable molecule will thus create a strong and symmetric hysteresis loop for the I-V characteristic of a pair of identical electrodes with molecules of this type trapped inside; see FIG. 3c, which depicts the full hysteresis loop. A distinct feature of the loop is that both its parts are traversed anti-clockwise (as in this example) or clockwise.

These molecules can be used as the active medium in a cross-point memory or as a switching element, for example.

The present invention is related to the quantum interference devices described in U.S. Pat. No. 5,903,010, "Quantum wire Switch and Switching Method", issued on May 11, 1999, to Flory and R. S. Williams and assigned to the same assignee as the present application. However, in the present invention, the weight of the wave-function moves from the "top" part (ring) of the molecule as a whole to the "bottom" part (ring), and vise versa, by changing the orientation of the dipole (as the molecule is depicted in FIGS. 2a–2b). The coupling between the two arms of the molecule remains very strong, and the electronic interference pattern (given by the molecular orbital weights) simply reflects about the middle of the molecule. Thus, the "switching" in the molecule, which is characterized by the hysteresis loop, can proceed by using the diode behavior of the I-V curve, stemming from the asymmetry of the molecule as a whole, not by qualitatively changing the nodes of the wave function.

The representative molecules, shown in Formula (I), may be prepared by a variety of techniques and employed in microscale and nanoscale applications. For example, a single monolayer molecular film can be grown on an electrode or wire, for example using Langmuir-Blodgett techniques or self-assembled monolayer (also called SAMs), such that the orientation or current-carrying axis of the molecules is perpendicular to the plane of the electrodes used to switch the molecules. Bottom and top electrodes may be deposited in the manner described by Collier et al, supra, or methods described in the above-enumerated related patent applications and issued patent.

The technology disclosed and claimed herein for forming crossed wires (micro-meter or nanometer) may be used to perform a variety of functions and to form a variety of useful devices and circuits for implementing computing on a microscale and even on a nanoscale. For example, applications include molecular wire crossbar interconnects (MWCI) for signal routing and communications, molecular wire crossbar memory (U.S. Pat. No. 6,128,214), molecular wire crossbar logic (MWCL) employing programmable logic arrays, a demultiplexer for a molecular wire crossbar network, and molecular wire transistors.

Figure 4:
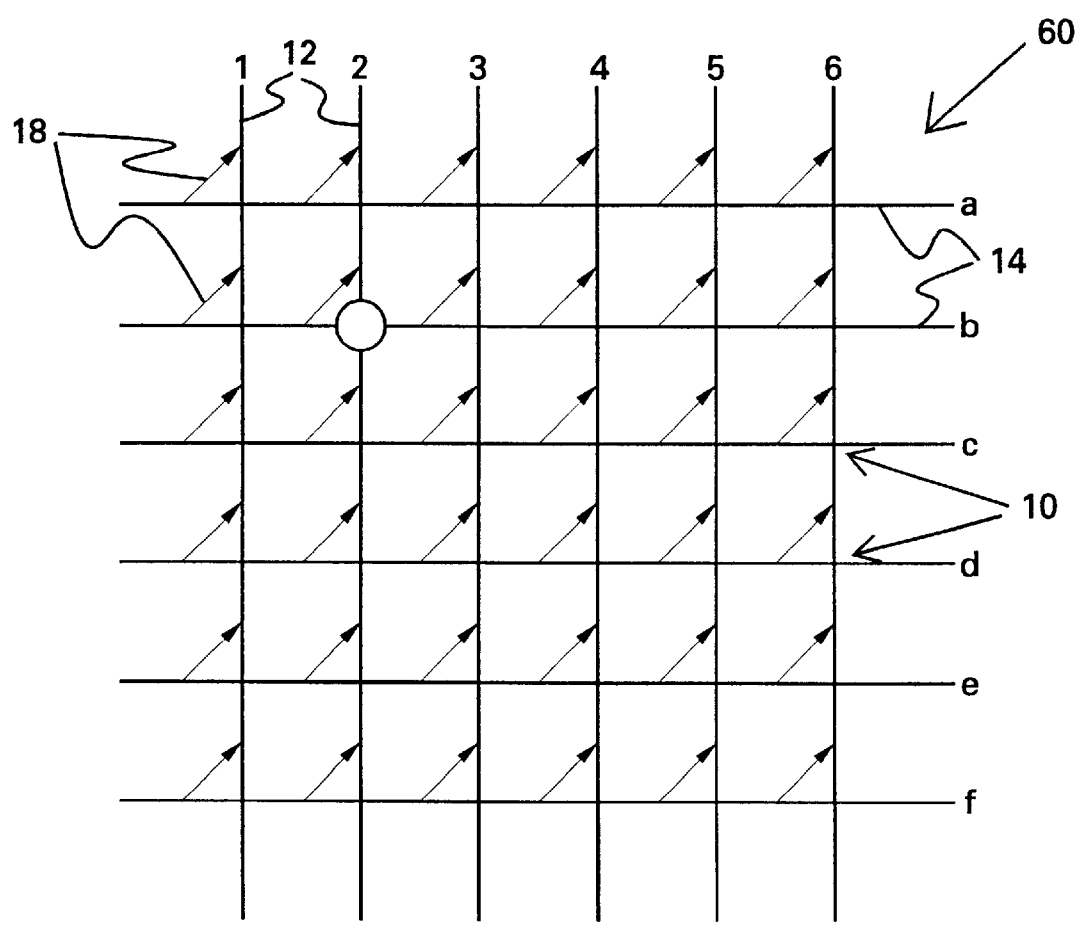
FIG. 4 is a schematic representation of a two-dimensional array of switches of the present invention, depicting a 6×6 crossbar switch.

As illustrated in FIG. 4, the switch 10 of the present can be replicated in a two-dimensional array to form a plurality, or array, 60 of switches to form a crossbar switch. FIG. 4 depicts a 6×6 array 60, but the invention is not so limited to the particular number of elements, or switches, in the array. Access to a single point, e.g., 2b, is done by impressing voltage on wires 2 and b to cause a change in the state of the molecular species 18 at the junction thereof, as described above. Thus, access to each junction is readily available for configuring only those pre-selected junctions in accordance with the teachings herein. Details of the operation of the crossbar switch array 60 are further discussed in above-referenced U.S. Pat. No. 6,128,214.

Industrial Applicability

The bistable molecules disclosed herein are expected to find use in micro-scale and nano-scale devices.

What is claimed is:

1. A method of fabricating a crossed-wire device comprising a pair of crossed wires which form a junction where one wire crosses another and at least one connector species connecting said pair of crossed wires in said junction, said junction having a functional dimension in nanometers, said method comprising (a) forming said first wire, (b) depositing said at least one connector species over at least a portion of said first wire, and (c) forming said second wire over said first wire so as to form said junction, wherein said at least one connector species comprises a bistable molecule having a general formula given by

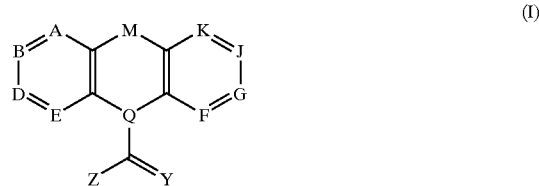

(I)

where the letters in Formula (I) mean any of the following:

A=CH; N; C-alkyl; C-halogen; C—OH; C—OR(ether); C—SR(thioether); C-amide; C-ester or thioester;

B=CH; N; C-alkyl; C-halogen; ; C—OH; C—OR(ether); C—SR(thioether); C-amide; C-ester or thioester;

D=CH; N; C-alkyl; C-halogen; C—OH; C—OR(ether); C—SR(thioether); C-amide; C-ester or thioester;

E=CH; N; C-alkyl; C-halogen; C—OH; C—OR(ether); C—SR(thioether); C-amide; C-ester or thioester;

F=CH; N; C-alkyl; C-halogen; C—OH; C—OR(ether); C—SR(thioether); C-amide; C-ester or thioester;

G=CH; N; C-alkyl; C-halogen; C—OH; C—OR(ether); C—SR(thioether); C-amide; C-ester or thioester;

J=CH; N; C-alkyl; C-halogen; C—OH; C—OR(ether); C—SR(thioether); C-amide; C-ester or thioester;

K=CH; N; C-alkyl; C-halogen; C—OH; C—OR(ether); C—SR(thioether); C-amide; C-ester or thioester;

M=$CH_2$; $CF_2$; $CCl_2$; $CHOCH_3$; CHOH; CHF; CO; CH=CH; $CH_2$—$CH_2$; S; O; NH; NR; NCOR; or NCOAr;

Q=CH; nitrogen; phosphorus; or boron;

Y=O or S; and

Z=R (H; alkyl); NHR; OR; SR; CHR—NHR; CHR—OR; CHR—SR; CHR—X (halogen); NR—NHR; NR—OR; or NR—SR.

2. The method of claim 1 wherein said bistable molecule has a formula given by

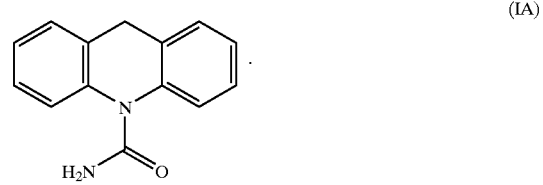

(IA)

3. A method of operating a crossed-wire device comprising a pair of crossed wires which form a junction where one wire crosses another and at least one connector species connecting said pair of crossed wires in said junction, said junction having a functional dimension in nanometers, said method comprising biasing both wires at least once with a first voltage sufficient to cause said connector species to switch its state, wherein said at least one connector species comprises a bistable molecule having a general formula given by

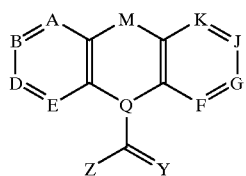

(I)

where the letters in formula (I) mean any of the following:

A=CH; N; C-alkyl; C-halogen; C—OH; C—OR(ether); C—SR(thioether); C-amide; C-ester or thioester;

B=CH; N; C-alkyl; C-halogen; ; C—OH; C—OR(ether); C—SR(thioether); C-amide; C-ester or thioester;

D=CH; N; C-alkyl; C-halogen; C—OH; C—OR(ether); C—SR(thioether); C-amide; C-ester or thioester;

E=CH; N; C-alkyl; C-halogen; C—OH; C—OR(ether); C—SR(thioether); C-amide; C-ester or thioester;

F=CH; N; C-alkyl; C-halogen; C—OH; C—OR(ether); C—SR(thioether); C-amide; C-ester or thioester;

G=CH; N; C-alkyl; C-halogen; C—OH; C—OR(ether); C—SR(thioether); C-amide; C-ester or thioester;

J=CH; N; C-alkyl; C-halogen; C—OH; C—OR(ether); C—SR(thioether); C-amide; C-ester or thioester;

K=CH; N; C-alkyl; C-halogen; C—OH; C—OR(ether); C—SR(thioether); C-amide; C-ester or thioester;

M=$CH_2$; $CF_2$; $CCl_2$; $CHOCH_3$; CHOH; CHF; CO; CH=CH; $CH_2$—$CH_2$; S; O; NH; NR; NCOR; or NCOAr;

Q=CH; nitrogen; phosphorus; or boron;

Y=O or S; and

Z=R (H; alkyl); NHR; OR; SR; CHR—NHR; CHR—OR; CHR—SR; CHR—X (halogen); NR—NHR; NR—OR; or NR—SR.

4. The method of claim 3 wherein said bistable molecule has a formula given by

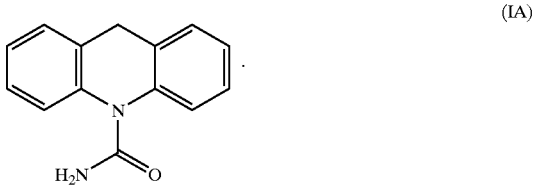

(IA)

* * * * *